US009441006B2

(12) United States Patent
Kvapil et al.

(10) Patent No.: US 9,441,006 B2
(45) Date of Patent: Sep. 13, 2016

(54) POLYMORPH OF 2-[4-[(METHYLAMINO)CARBONYL]-1H-PYRAZOL-1-YL]ADENOSINE

(71) Applicant: Farmak, a.s., Olomouc (CZ)

(72) Inventors: Lubomir Kvapil, Slatinice (CZ); Pavel Hradil, Hlusovice (CZ); Martin Grepl, Hlusovice (CZ); Petr Slezar, Olomouc (CZ); Barbora Dvorakova, Most (CZ)

(73) Assignee: Farmak, a.s., Olomouc (CZ)

( * ) Notice: Subject to any disclaimer, the term of this patent is extended or adjusted under 35 U.S.C. 154(b) by 153 days.

(21) Appl. No.: 13/929,005

(22) Filed: Jun. 27, 2013

(65) Prior Publication Data

US 2014/0323712 A1     Oct. 30, 2014

(30) Foreign Application Priority Data

Apr. 29, 2013  (CZ) .................................... 2013-320

(51) Int. Cl.
| C07H 19/00 | (2006.01) |
| C07H 19/19 | (2006.01) |
| C07H 19/16 | (2006.01) |
| C07H 1/06 | (2006.01) |
| C07H 1/00 | (2006.01) |
| C07H 19/167 | (2006.01) |

(52) U.S. Cl.
CPC ................ *C07H 19/16* (2013.01); *C07H 1/00* (2013.01); *C07H 1/06* (2013.01); *C07H 19/167* (2013.01)

(58) Field of Classification Search
CPC .......... C07H 19/16; C07H 1/06; C07H 1/00; C07H 19/167
See application file for complete search history.

(56) References Cited

U.S. PATENT DOCUMENTS

| 3,493,604 | A | 2/1970 | Nelson |
| 6,403,567 | B1 | 6/2002 | Zablocki et al. |
| 6,514,949 | B1 | 2/2003 | Linden et al. |
| 6,642,210 | B1 * | 11/2003 | Zablocki et al. ............... 514/46 |
| 7,037,935 | B2 * | 5/2006 | Iding .................. C07D 207/277 514/423 |
| 7,671,192 | B2 * | 3/2010 | Zablocki et al. .......... 536/27.11 |
| 7,732,595 | B2 * | 6/2010 | Zablocki et al. .......... 536/27.11 |
| 7,846,956 | B2 | 12/2010 | Mitsudera et al. |
| 7,956,179 | B2 * | 6/2011 | Zablocki et al. .......... 536/27.11 |
| 8,106,183 | B2 * | 1/2012 | Zablocki et al. .......... 536/27.11 |
| 8,268,988 | B2 * | 9/2012 | Zablocki et al. .......... 536/27.11 |
| 8,470,801 | B2 * | 6/2013 | Belardinelli et al. ........... 514/46 |
| 8,524,883 | B2 * | 9/2013 | Zablocki et al. .......... 536/27.11 |
| 8,859,522 | B2 * | 10/2014 | Wooldridge et al. ........... 514/46 |
| 2004/0106650 | A1 | 6/2004 | Iding et al. |
| 2010/0063262 | A1 | 3/2010 | Tateishi et al. |
| 2010/0267953 | A1 | 10/2010 | Zablocki et al. |
| 2014/0213539 | A1 * | 7/2014 | Zablocki et al. ............... 514/45 |

FOREIGN PATENT DOCUMENTS

| WO | WO 2005/068432 | 7/2005 |
| WO | WO 2007/092372 | 8/2007 |
| WO | WO 2008/143667 | 11/2008 |
| WO | WO 2012/149196 | 11/2012 |
| WO | WO 2013/023626 | 2/2013 |
| WO | WO 2013/026424 | 2/2013 |

OTHER PUBLICATIONS

Zablocki et al., 2-substituted pi system derivatives of adenosine that are coronary vasodilators acting via the $A_{2A}$ adenosine receptor, nucleosides, nucleotides & nucleic acids, vol. 20 (4-7), pp. 343-360, 2001.

Sorbera, Regadenoson adenosine $A_{2A}$ agonist adjunct for myocardial perfusion imaging, Drugs of The Future, vol. 29, No. 10, pp. 998-1002, Jan. 1, 2004.

Palle et al., Structure-Affinity Relationships of the Affinity of 2-Pyrazolyl Adenosine Analogues for the Adenosine $A_{2A}$ Receptor, Bioorganic & Medicinal Chemistry Letters, vol. 12, pp. 2935-2939, 2002.

Bertz et al., New Preparations of Ethyl 3,3-Diethoxypropionate and (Ethoxycarbonyl)malondialdehyde, Cu(I)-Catalyzed Acetal Formation form a Conjugated Triple Bond, Journal of Organic Chemistry, vol. 47, pp. 2216-2217, 1982.

(Continued)

*Primary Examiner* — Lawrence E Crane
(74) *Attorney, Agent, or Firm* — Pearl Cohen Zedek Latzer Baratz LLP

(57) ABSTRACT

The invention relates to a compound which is, 2-[4-[(methylamino)carbonyl]-1H-pyrazol-1-yl]adenosine, which is a selective A2A adenosine receptor agonist in myocardial imaging. The new polymorph of 2-[4-[(methylamino)carbonyl]-1H-pyrazol-1-yl]adenosine (designated as polymorph E) is characterized by an X-ray diffraction pattern of X-RPD showing the following reflections at 2 Theta=5.8°, 12.3°, 15.9°, 17.3°, 20.5°, 22.6°, 23.6°, 27.7°, and 29.2°; and further characterized by a DSC scan showing marked endotherm in the range of 258 to 264° C.; and further characterized by a specific IR spectra. The invention further relates to a method of preparing the polymorph by recrystallization from other polymorphic forms of 2-[4-[(methylamino)carbonyl]-1H-pyrazol-1-yl]adenosine by a procedure comprising the following operations: mixing of 2-[4-[(methylamino)carbonyl]-1H-pyrazol-1-yl]adenosine with a polar aprotic solvent, preferably with dimethylsulfoxide, and heating to form a saturated solution; cooling of the saturated solution with formation of a turbid solution of 2-[4-[(methylamino)carbonyl]-1H-pyrazol-1-yl]adenosine; addition of the turbid solution of 2-[4-[(methylamino)carbonyl]-1H-pyrazol-1-yl] adenosine to a protic solvent, preferably methanol, with separation of a gel-like precipitate; heating of the separated gel-like precipitate in the protic solvent to a boil with formation of a suspension of polymorph E; and cooling of the suspension, isolation and drying of polymorph E.

7 Claims, 4 Drawing Sheets

(56) References Cited

OTHER PUBLICATIONS

Schaeffer et al., Synthesis of Potential Anticancer Agents, XIV, Ribosides of 2,6-Disubstituted Purines, Journal of American Chemistry Socity, vol. 80, pp. 3738-3742, 1958.
Zhichkin et al., A General Procedure for the Synthesis of 2-Substituted Pyrimidine-5-Carboxylic Esters, Synthesis, No. 6, pp. 720-722, 2002.
March Jerry, Advanced Organic Chemistry, pp. 423-424, 4$^{th}$ edition, 1992.
US Office Action for U.S. Appl. No. 14/239,261 dated Nov. 13, 2015.
U.S Office Action U.S. Appl. No. 14/239,788 dated Nov. 5, 2015.

* cited by examiner

POLYMORPH OF 2-[4-[(METHYLAMINO)CARBONYL]-1H-PYRAZOL-1-YL]ADENOSINE

CROSS REFERENCE TO RELATED APPLICATIONS

This application claims the benefit of Czech Republic application Serial No. PV 2013-320, which was filed on Apr. 29, 2013, and is incorporated herein by reference.

TECHNICAL FIELD

The invention relates to a new polymorph of 2-[4-[(Methylamino)carbonyl]-1H-pyrazol-1-yl]adenosine of formula I

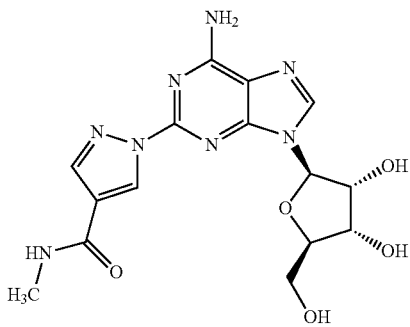

and a method of its preparation. 2-[4-[(Methylamino)carbonyl]-1H-pyrazol-1-yl]adenosine in the form of hydrate is known as regadenoson, which is used as coronary vasodilator for diagnostic purposes in radionuclide examination of heart.

BACKGROUND ART

The patent literature describes several different polymorphs of 2-[4-[(methylamino)-carbonyl]-1H-pyrazol-1-yl]adenosine of formula I.

PCT application WO 2008/143667 describes polymorphs A, B, C, and the amorphous form. Polymorph A is prepared by crystallization of 2-[4-[(methylamino)carbonyl]-1H-pyrazol-1-yl]adenosine from protic solvents or their mixtures with water (for example ethanol or an ethanol/water mixture) or by crystallization from polar aprotic solvents or their mixtures with water (for example a dimethylsulfoxide/water mixture). Polymorph A is a monohydrate and, contrary to other as yet known polymorphs, it is relatively stable.

Polymorph B is prepared by concentrating 2-[4-[(methylamino)carbonyl]-1H-pyrazol-1-yl]adenosine dissolved in trifluoroethanol. The preparation of this polymorph is difficult to reproduce and X-RPD shows broad peaks that are difficult to measure.

Polymorph C is prepared by heating of a suspension of 2-[4-[(methylamino)carbonyl]-1H-pyrazol-1-yl]adenosine in acetonitrile at 60° C. for prolonged periods. This polymorph contains variable amount of water and is converted to unstable forms by heating.

The amorphous form is prepared by heating polymorph A to a temperature of 200° C. The amorphous form is unstable and in presence of air humidity it forms variable hydrates.

PCT application WO 2012/149196 describes preparation of polymorph D by a relatively complicated procedure. First, a "cross coupling" reaction of 2-fluoroadenosine with N-methylpyrazol-4-carboxamide in an acetonitrile/dimethylsulfoxide mixture provides crude 2-[4-[(methylamino)carbonyl]-1H-pyrazol-1-yl]adenosine, which is then purified by reverse-phase chromatography using a methanol/water mixture. After concentrating at 150° C. under reduced pressure, polymorph D is obtained as a white solid substance containing variable amounts of water.

It is known that polymorphs of one medicinal substance can have different physico-chemical properties, such as solubility, stability, density, and compressibility. As a result, they can have different pharmacological properties and also different biological availability. Therefore, deep knowledge of polymorphs is required from the authorities carrying out control of drugs, medicinal substances, and diagnostics (U.S. Food and Drug Administration).

SUMMARY OF THE INVENTION

The present invention relates to a new stable polymorph of 2-[4-[(methylamino)carbonyl]-1H-pyrazol-1-yl]adenosine (hereinafter referred to as polymorph E) and a method of its preparation.

Polymorph E is characterized by X-ray powder diffraction (hereinafter XRPD only) and differential scanning calorimetry (hereinafter DSC only).

Polymorph E is characterized by the following reflections in XRPD diffraction pattern: 2 Theta=5.8°, 12.3°, 15.9°, 17.3°, 20.5°, 22.6°, 23.6°, 27.7°, and 29.2° (see FIG. 1).

In addition, polymorph E is characterized by DSC showing a marked endotherm transition between 258 and 264° C. (see FIG. 2).

Polymorph E is further characterized by IR spectra (see FIG. 3).

Regadenoson is used as an injection form in aqueous solutions. Due to the fact that regadenoson in all its known polymorphic forms shows poor water solubility, this fact has been paid a great attention to.

Solubility of polymorph E has been determined experimentally in comparison with polymorph A; it has been found that, at different temperatures, solubility of both polymorphs in water is practically the same. However, it has been surprisingly found that the dissolution rate of polymorph E in water is markedly higher than that of polymorph A. Using the Lasentec FBRM instrument for measuring particle size distribution (manufactured by Lasentec Product Group, model D600 VL, software FBRM version 6.7.0), dissolution rates of polymorph A and polymorph E have been experimentally compared. Equal amounts of both polymorphs (165 mg) were dissolved in the same amounts of water (500 ml) under identical conditions (dissolving regime, stirrer revolutions, etc.). The curves depicting dissolution rates of the two polymorphs are shown in FIG. 4. It is obvious that the dissolution rate of polymorph E is approximately twofold. Polymorph E is completely dissolved within about 45 minutes, whereas the same amount of polymorph A is, under same conditions, dissolved after about 90 minutes.

Practically, this finding is very important as it enables a quicker preparation of injectable solutions and, at the same time, it increases capacity of the production unit. Moreover, it shortens thermal exposition of the dissolved 2-[4-[(methylamino)carbonyl]-1H-pyrazol-1-yl]adenosine and thus substantially reduces formation of possible decomposition products.

Polymorph E of 2-[4-[(methylamino)carbonyl]-1H-pyrazol-1-yl]adenosine of formula I represents a relatively stable polymorph complying with the tests according to ICH Guideline Stability Testing of New Drug Substances and Products Q1A (R2).

Polymorph E of 2-[4-[(methylamino)carbonyl]-1H-pyrazol-1-yl]adenosine of formula I contains residual solvents in compliance with ICH Guideline for Residual Solvents Q3C (for example, content of methanol max. 3000 ppm and content of dimethylsulfoxide max. 5000 ppm) and variable amount of water (usually up to 1.0%).

Polymorph E can be prepared from all known polymorphic forms, or their mixtures, or directly from the concentrated reaction solution by means of a simple and reproducible procedure, comprising the following operations:

Mixing of 2-[4-[(methylamino)carbonyl]-1H-pyrazol-1-yl]adenosine with a polar aprotic solvent, preferably with dimethylsulfoxide, and heating with formation of a saturated solution;

Cooling of the saturated solution with formation of a turbid solution of 2-[4-[(methylamino)carbonyl]-1H-pyrazol-1-yl]adenosine;

Addition of the turbid solution of 2-[4-[(methylamino)carbonyl]-1H-pyrazol-1-yl]adenosine to a protic solvent, preferably methanol, with falling out of a gel-like precipitate;

Heating up of the fallen-out gel-like precipitate in the protic solvent to the boil with formation of a suspension of polymorph E;

Cooling of the suspension, isolation, and drying of polymorph E.

The procedure according to the submitted invention brings several benefits.

2-[4-[(methylamino)carbonyl]-1H-pyrazol-1-yl]adenosine is a substance of generally poor solubility in common organic solvents; the few solvents in which it dissolves include aprotic solvents, such as dimethylacetamide, dimethylformamide, N-methylpyrrolidone, sulfolane, or dimethylusulfoxide. Particularly beneficial is practically non-toxic dimethylsulfoxide. The above mentioned solvents can be used in a wide range of temperatures, from room temperature virtually up to the temperature of 150° C., preferably in the temperature range from 30° C. to 100° C. Following the subsequent cooling down with formation of the turbid solution, the addition of protic solvents, preferably methanol, results in separation of the gel-like precipitate which is, by further heating, converted to the desired polymorph E.

In comparison with other polymorphs (particularly polymorphs B, C, and the amorphous form), polymorph E according to the present invention represents a relatively stable polymorph.

In comparison with other polymorphs, this polymorph shows very good rheological properties, it can be easily filtered, is free flowing, and has low electrostatic charge.

Polymorph E shows higher dissolution rate in water, which is beneficial concerning its use in the production of injectable forms.

EXAMPLES

Figure 1:
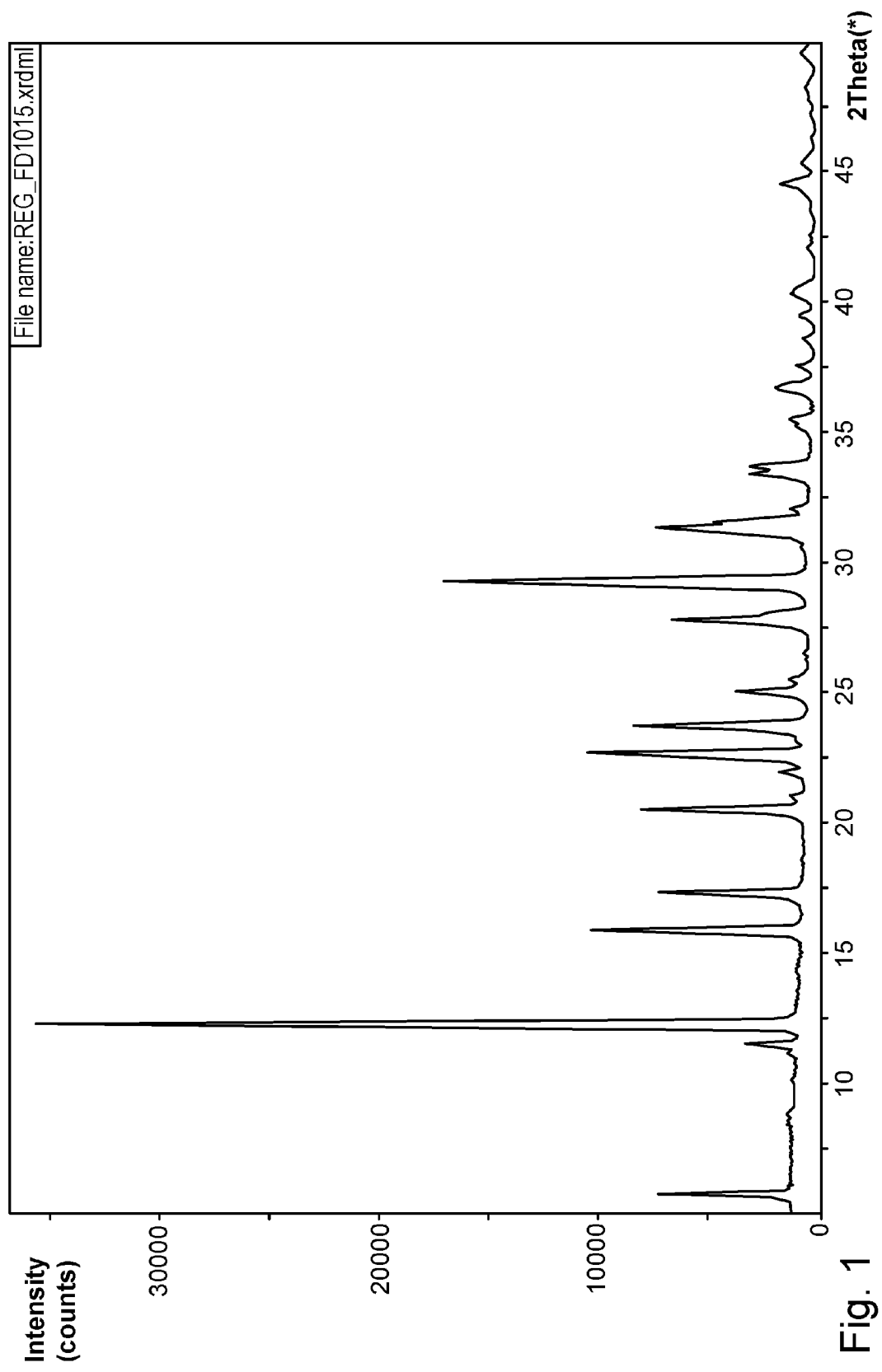
FIG. 1 shows an XRPD diffraction pattern of polymorph E according to the invention.

The essence of carrying out the invention is explained in details in the following examples. These examples are of illustrative character only and by no means do they limit the scope of the invention.

To make the description of the preparation of polymorph E more illustrative, the description of the preparation in Examples 1 and 2 is extended by the description of the preparation of the amorphous form and polymorph A according to our PCT application WO 2013/026424 (A1).

XRPD was measured in an X'Pert PRO MPD instrument (PANalytical, Netherlands) with Co X-ray tube ($\lambda$=1.78901 Å, U=40 kV, I=30 mA). Samples were put on diffraction-free Si-plates and measured in the Bragg-Brentan parafocusing geometry with step size of 0.0167° 2 Theta in the range of 2 Theta angles 5°-50°. The diffraction scans were processed using the program High-Score Plus (PANalytical). Positions of diffraction peaks and instrumental expansion of diffractions were controlled using SRM640 (Si) and SRM660 (LaB6) standards from NIST.

DSC measurements were performed using a Perkin Elmer model Pyris Diamond DSC calorimeter with evaluation by Pyris software version 5.0. The samples were scanned in open aluminium pans in the nitrogen atmosphere. The temperature range was set from 50° C. with a heating rate of 5° C./min.

IR spectra were measured by the ATR method on a ZnSe crystal using a Nicolet IS 10 instrument (Thermo Scientific).

Example 1

A suspension of 1 g of 2-(4-methoxycarbonylpyrazol-1-yl)adenosine in 10 ml of 40% methylamine in methanol is stirred in a closed flask at 20° C. until formation of a solution (3 to 5 hours). The produced solution is left to stand at the given temperature for additional 15 hours. The solution is then filtered with active charcoal and the filtrate is concentrated in vacuo. The evaporation residue, which is the amorphous form of 2-[4-[(methylamino)carbonyl]-1H-pyrazol-1-yl]adenosine, is dissolved in 2 ml of dimethylsulfoxide and left to cool down freely to room temperature. The resulting turbid solution is added to 20 ml of methanol. The separated gel-like precipitate is stirred under the boil for 1.5-2.5 hours, wherein a powder-like suspension is formed. After cooling down, sucking off, and drying, 0.8 g of 2-[4-[(methylamino)carbonyl]-1H-pyrazol-1-yl]adenosine polymorph E is obtained.

XRPD diffraction pattern: 2 Theta=5.8°, 12.3°, 15.9°, 17.3°, 20.5°, 22.6°, 23.6°, 27.7°, and 29.2°.

The DSC trace shows an endotherm at 259.2° C.

Example 2

A suspension of 1 g of 2-(4-methoxycarbonylpyrazol-1-yl)adenosine in 10 ml of 40% methylamine in methanol is stirred in a closed flask at 20° C. until formation of a solution (about 3 to 5 hours). The formed solution is left to stand at the given temperature for additional 15 hours. The solution is then filtered with active charcoal and the filtrate is carefully partially concentrated, wherein a gel-like precipitate of anhydrous 2-[4-[(methylamino)carbonyl]-1H-pyrazol-1-yl]adenosine is separated. By gradual addition of 10 ml of water, the gel-like precipitate converts to a fine powder-like precipitate, which, after stirring up, is sucked off, thoroughly washed with water, then with methanol, and vacuum-dried to constant weight.

In this way, 0.9 g of 2-[4-[(methylamino)carbonyl]-1H-pyrazol-1-yl]adenosine monohydrate (polymorph A) is obtained; which is dissolved in 1.8 ml of dimethylsulfoxide and left to freely cool down to room temperature. The formed turbid solution is added to 18 ml of methanol at 50 to 60° C. A gel-like precipitate separates, which is stirred under the boil for 1.5-2.5 hours, wherein a powder-like suspension is formed. After cooling down, sucking off, and drying, 0.75 g of 2-[4-[(methylamino)carbonyl]-1H-pyrazol-1-yl]adenosine polymorph E is obtained.

XRPD diffraction pattern: 2 Theta=5.8°, 12.3°, 15.9°, 17.3°, 20.5°, 22.6°, 23.6°, 27.7°, and 29.2°.

The DSC record shows an endotherm at 260.7° C.

Example 3

A suspension of 2 g of 2-[4-[(methylamino)carbonyl]-1H-pyrazol-1-yl]adenosine polymorph C (prepared according to PCT/US2007/069190, page 10) is dissolved in 3 ml of dimethylsulfoxide and left to cool down freely to room temperature. The formed turbid solution is poured to 30 ml of methanol at 50 to 60° C. A gel-like precipitate separates, which is stirred under the boil for 1 hour, wherein a powder-like suspension forms, which is cooled down to room temperature. After cooling down, sucking off, and drying, 1.75 g of 2-[4-[(methylamino)carbonyl]-1H-pyrazol-1-yl]adenosine polymorph E is obtained.

XRPD diffraction pattern: 2 Theta=5.8°, 12.3°, 15.9°, 17.3°, 20.5°, 22.6°, 23.6°, 27.7°, and 29.2°.

The DSC record shows an endotherm at 259.3° C.

We claim:

1. A compound that is polymorph E of 2-[4-[(methylamino)carbonyl]-1H-pyrazol-1-yl]adenosine of formula I,

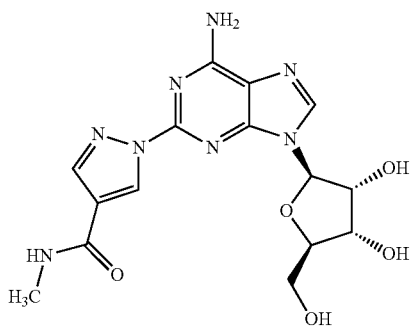

having an X-ray diffraction pattern of X-RPD showing the following reflections at 2 Theta=5.8°, 12.3°, 15.9°, 17.3°, 20.5°, 22.6°, 23.6°, 27.7°, and 29.2°.

2. The compound of claim 1 that is polymorph E of 2-[4-[(methylamino)carbonyl]-1H-pyrazol-1-yl]adenosine of formula I, having a X-ray diffraction pattern of X-RPD according to FIG. 1.

3. The compound of claim 1 that is polymorph E of 2-[4-[(methylamino)carbonyl]-1H-pyrazol-1-yl]adenosine of formula I, wherein a differential scanning calorimetry DSC shows a showing marked endotherm in the range of 258 to 264° C.

Figure 2:
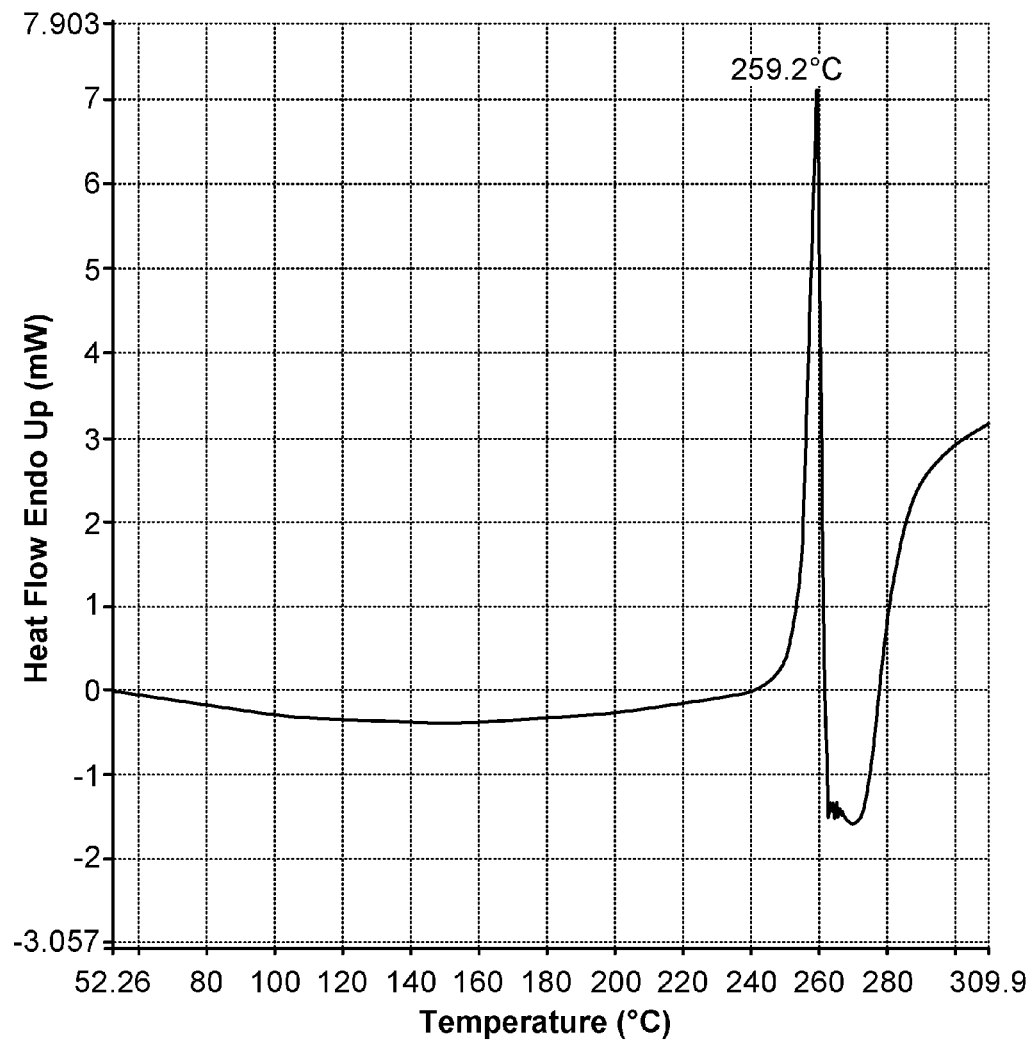
FIG. 2 is a DSC record of polymorph E according to the invention.

4. The compound of claim 1 that is polymorph E of 2-[4-[(methylamino)carbonyl]-1H-pyrazol-1-yl]adenosine of formula I, having a DSC scan according to FIG. 2.

Figure 3:
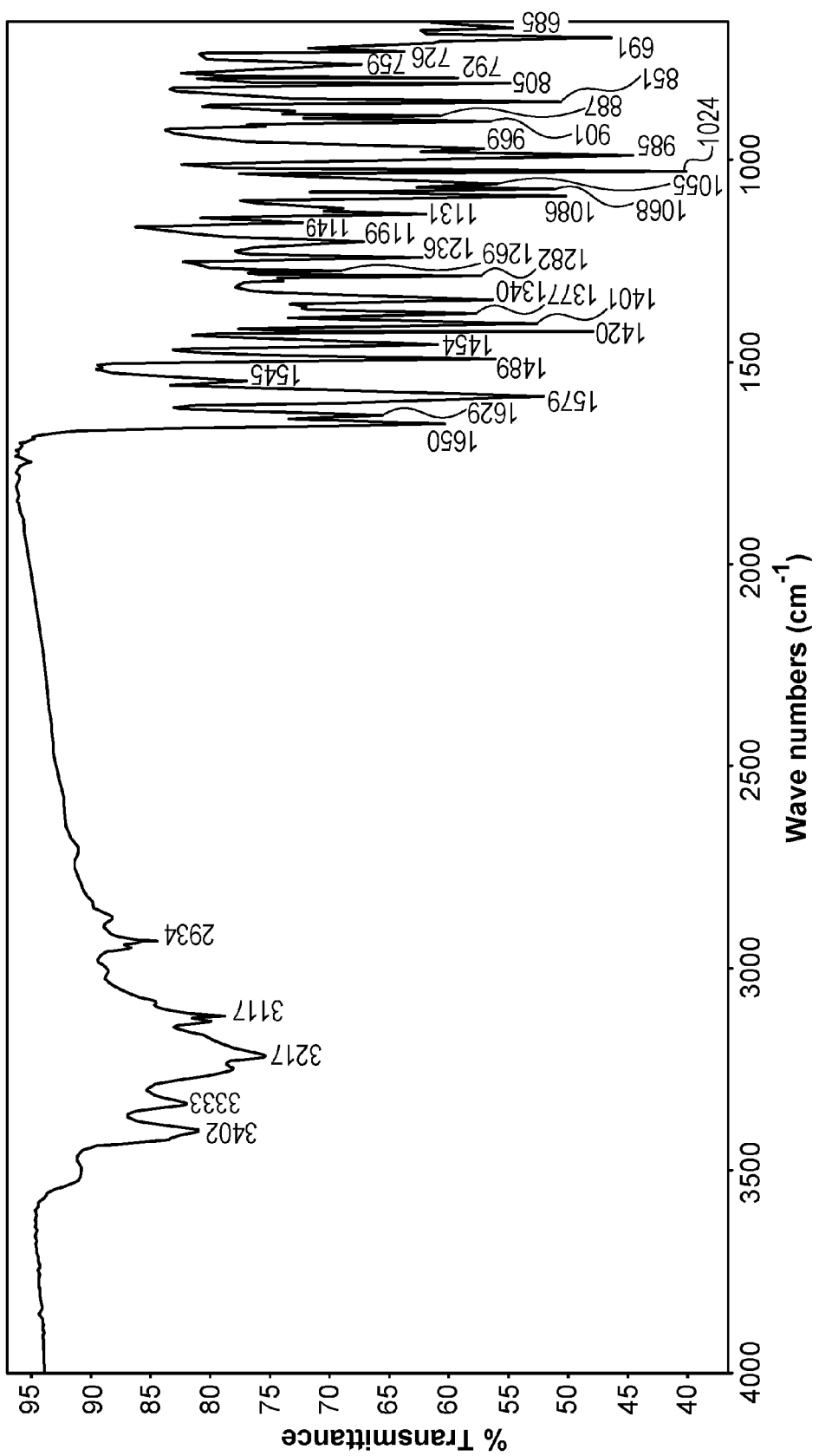
FIG. 3 shows an IR spectrum of polymorph E according to the invention.
Figure 4:
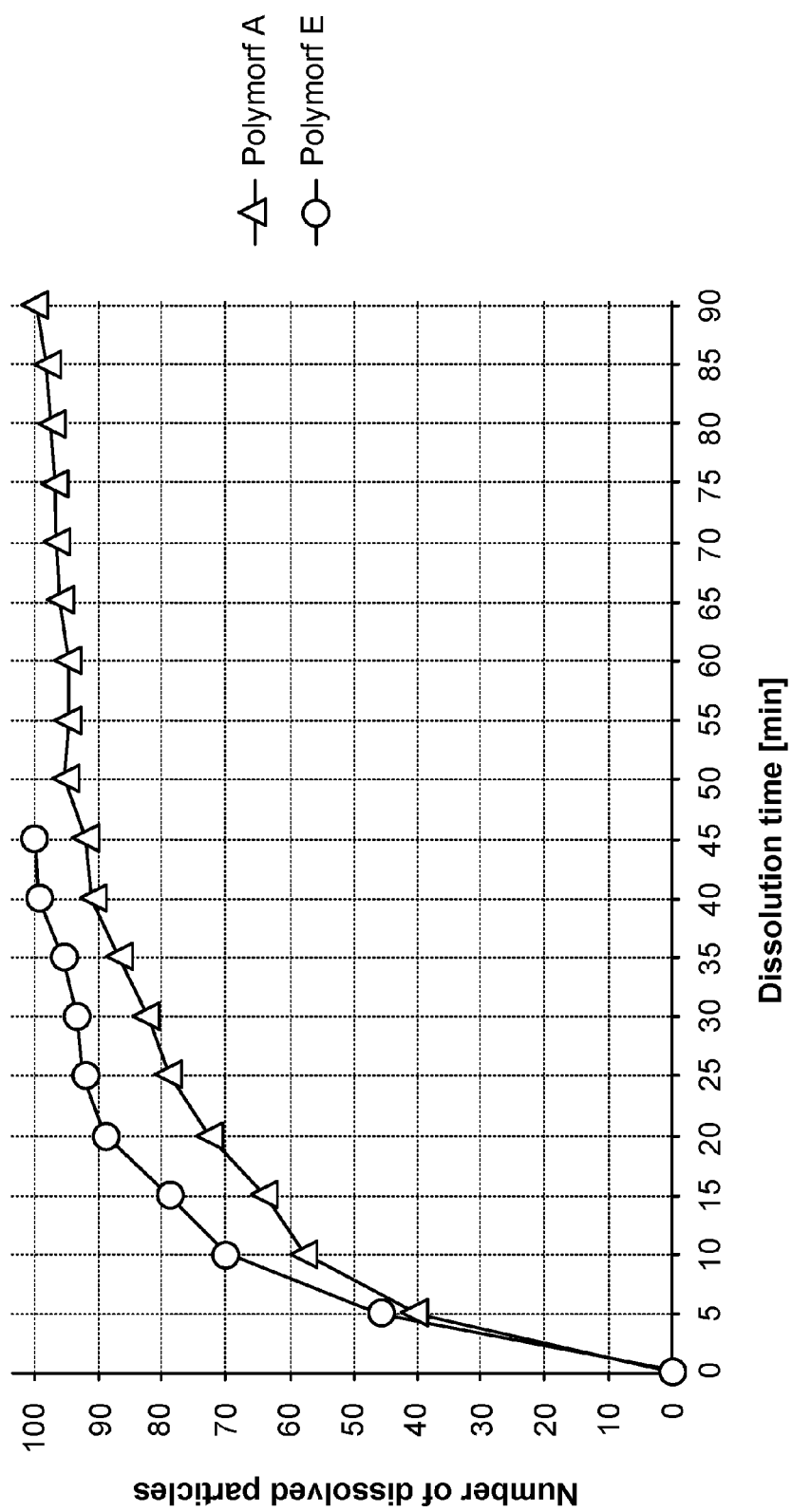
FIG. 4 depicts curves of dissolution rates of polymorph E according to the invention in comparison with polymorph A.

5. The compound of claim 1 that is polymorph E of 2-[4-[(methylamino)carbonyl]-1H-pyrazol-1-yl]adenosine of formula I, having an IR spectra according to FIG. 3.

6. A method of preparing polymorph E of 2-[4-[(methylamino)carbonyl]-1H-pyrazol-1-yl]adenosine of formula I,

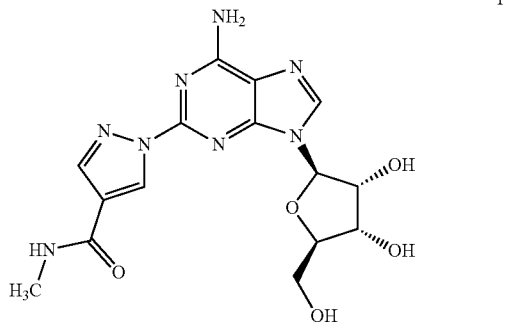

comprising the steps of:
mixing 2-[4-[(methylamino)carbonyl]-1H-pyrazol-1-yl]adenosine with a polar aprotic solvent, selected from the group consisting of dimethylacetamide, dimethylformamide, N-methylpyrrolidone, sulfolane, or dimethylsulfoxide, and heating to form a saturated solution;
cooling the saturated solution with formation of a turbid solution of 2-[4-[(methylamino)carbonyl]-1H-pyrazol-1-yl]adenosine;
adding the turbid solution of 2-[4-[(methylamino)carbonyl]-1H-pyrazol-1-yl]adenosine to a methanol with separation of a gel-like precipitate;
heating the separated gel-like precipitate with the methanol to a boil with formation of a suspension of polymorph E;
cooling the suspension, isolating and drying the polymorph E.

7. The method according to claim 6, wherein said polar aprotic solvent is dimethylsulfoxide.

* * * * *

UNITED STATES PATENT AND TRADEMARK OFFICE
CERTIFICATE OF CORRECTION

Page 1 of 1

PATENT NO. : 9,441,006 B2
APPLICATION NO. : 13/929005
DATED : September 13, 2016
INVENTOR(S) : Lubomir Kvapil et al.

It is certified that error appears in the above-identified patent and that said Letters Patent is hereby corrected as shown below:

In the Claims

In Column 6 Line 8 please omit the word "showing".

Signed and Sealed this
Third Day of January, 2017

Michelle K. Lee
*Director of the United States Patent and Trademark Office*